United States Patent [19]
Heineke et al.

[11] Patent Number: 5,753,583
[45] Date of Patent: May 19, 1998

[54] SUPPORTED PALLADIUM CATALYST

[75] Inventors: Daniel Heineke, Ludwigshafen; Klemens Flick, Herxheim; Martin Wünsch, Ellerstadt, all of Germany

[73] Assignee: BASF Aktiengesellschaft, Ludwigshafen, Germany

[21] Appl. No.: 580,502

[22] Filed: Dec. 28, 1995

[51] Int. Cl.$^6$ ........................................ B01J 23/44
[52] U.S. Cl. .......................... 585/326; 585/327; 585/332
[58] Field of Search .................................. 502/326, 327, 502/332, 523

[56] References Cited

U.S. PATENT DOCUMENTS

| | | |
|---|---|---|
| 4,048,092 | 9/1977 | Davies . |
| 4,493,906 | 1/1985 | Couvillion . |
| 4,577,047 | 3/1986 | Hudson . |
| 4,839,329 | 6/1989 | Ihm et al. . |
| 4,906,800 | 3/1990 | Henry et al. . |
| 5,063,194 | 11/1991 | Broecker . |
| 5,102,853 | 4/1992 | Chattha . |
| 5,376,344 | 12/1994 | Chattha . |
| 5,525,570 | 6/1996 | Chakraborty . |

FOREIGN PATENT DOCUMENTS

| | | |
|---|---|---|
| A-2128162 | 1/1995 | Canada . |
| 64301 | 11/1982 | European Pat. Off. . |
| 89252 | 9/1983 | European Pat. Off. . |
| A-412415 | 2/1991 | European Pat. Off. . |
| A-430435 | 6/1991 | European Pat. Off. . |
| A-503470 | 9/1992 | European Pat. Off. . |
| A-634214 | 1/1995 | European Pat. Off. . |
| 1284403 | 8/1969 | Germany . |

OTHER PUBLICATIONS

Chemical Abstracts, vol. 82 (1975): 169991c; Abstract of JP-B 80/047015, Kageyama et al.

*Primary Examiner*—Glenn Caldarola
*Assistant Examiner*—Bekir L. Yildirim
*Attorney, Agent, or Firm*—John H. Shurtleff

[57] ABSTRACT

A supported palladium catalyst having a palladium content of from 0.001 to 2 wt %, in which palladium is present, substantially in the absence of promotor metal, in the form of a layer having a thickness of less than 5000 nm forming a shell around the support, in which the palladium is applied in the form of a sol to a support by impregnation, or by spraying on to a heated support, and the use of said catalyst for the hydrogenation of acetylenes and dienes.

11 Claims, No Drawings

SUPPORTED PALLADIUM CATALYST

The present invention relates to supported palladium catalysts having a palladium content of from 0.001 to 2 wt %, in which the palladium is present, substantially in the absence of promotor metal, in the form of a layer having a thickness of less than 5000 nm forming a shell around the support, the palladium having been applied to the support as a sol by impregnation or by spraying on to a heated support, and to the use thereof for the hydrogenation of acetylenes and dienes.

Acetylenes and dienes are, due to their tendency to undergo polymerization or their pronounced proneness to form complexes over transition metals, undesirable materials in various industrially important syntheses, since acetylenes and dienes have a strongly deleterious effect on the catalysts used in this reaction. For example, the acetylene present in the $C_2$ stream of a steam cracker interferes with the polymerization of ethylene, so that the acetylene content in the $C_2$ stream must be lower than 1 ppm. Also, the $C_3$ stream coming from a steam cracker and containing, apart from propylene, from 2 to 3% of propadiene (PD) and approximately the same amount of propine (methyl acetylene, MA), must be purified prior to polymerization to polypropylene. The total content of acetylenes and dienes is reduced to less than 20 ppm by hydrogenation. Both of the hydrocarbon streams are purified in industrial practice by selective hydrogenation over heterogeneous noble metal catalysts on ceramic supports. Stringent demands are placed on the hydrogenation catalysts used as regards their selectivity and activity, as the hydrogenation should be accomplished without loss of ethylene or propylene except for a small, tolerable residual content of the acetylenes and dienes.

To this end promoted or non-promoted noble metal catalysts, mostly containing palladium on $Al_2O_3$ supports having a small surface area and having contents of active component(s) of from 0.01 to 1 wt % have been developed.

Chem. Abstracts, Vol. 82, 169,991 (JP-B 80/047015) describes the use of 0.05 wt % of palladium on macroporous $Al_2O_3$ supports having a surface area (BET) of from 0.1 to 2 $m^2/g$ as being advantageous. Using these catalysts, the acetylene content can be lowered to 10 ppm.

U.S. Pat. No. 4,493,906 discloses the use of finely divided copper on $\gamma$-$Al_2O_3$ which contains up to 35% of $\alpha$-$Al_2O_3$. The $\gamma$-$Al_2O_3$ used has a surface area of from 68 to 350 $m^2/g$ and 40 to 98% of the pores have a pore diameter of from 4 to 12 nm whilst 2 to 25% exhibit a pore diameter of from 100 to 1000 nm. Also bimetallic catalysts are known to have been used for the selective hydrogenation of acetylene.

EP-A 64,301 discloses the use of Pd/Ag catalysts containing from 0.01 to 0.025 wt % of Pd and from 2 to 6 times as much Ag based on palladium on $\alpha$-$Al_2O_3$ having a surface area of from 3 to 7 $m^2/g$ and a pore diameter of from 685 to 2270 Å. These catalysts are distinguished by a lower sensitivity to CO and longer on-stream times.

Pd/Au catalysts containing from 0.03 to 1 wt % of palladium and from 0.003 to 0.3 wt % of gold on $Al_2O_3$ supports and having a surface area of from 1 to 100 $m^2/g$ are disclosed in EP-A 89,252. They are described as being sensitive to poisoning and as having a low tendency to form oligomers in the presence of acetylene.

U.S. Pat. No. 4,577,047 reveals Pd/Cr catalysts containing from 0.01 to 0.5 wt % of palladium in a molar ratio of palladium to chromium of 0.5:1 to 2:1 on $Al_2O_3$ supports having small surface areas of less than 5 $m^2/g$.

U.S. Pat. No. 4,906,800 reveals that the selectivity of a Lindlar catalyst ($Pd/Pb/CaCO_3$) at temperatures higher than 100° C. can be improved by special pretreatment involving a series of different oxidation and reduction steps.

Furthermore, it is generally known that apart from $Al_2O_3$ other supports for noble metal-containing catalysts are possible for selective hydrogenation of acetylene.

U.S. Pat. No. 4,839,329 discloses the use of palladium on $TiO_2$ having a surface area of from 30 to 60 $m^2/g$ and DE-A 1,284,403 the use of Pd/Zn on $SiO_2$ as catalyst for the selective hydrogenation of acetylene.

It is well known that it is possible to add carbon monoxide to the reaction mixture in the hydrogenation of acetylene, in order to increase the selectivity of the catalyst. The drawback of these processes is that the selectivity-improving action of the carbon monoxide is highly dependent on temperature. Thus steep temperature gradients in the catalyst bed cause deterioration of the selectivity. Moreover, the higher working temperatures necessary for the metered introduction of CO induce an increased formation of undesirable polymers (green oil).

The previously described catalysts for the selective hydrogenation of acetylenes and dienes are generally prepared by impregnating an inert support with an aqueous solution of a palladium salt, or a mixture of a palladium salt with a salt of the promotor or by successive impregnation with aqueous solutions of the salts containing active components or promotor, followed by drying and calcination at elevated temperatures.

The previously described catalysts have the drawback that as the content of promotor increases the selectivity indeed rises but the activity falls steeply. Thus in order to achieve satisfactory activities high temperatures are necessary.

It is thus an object of the present invention to overcome the aforementioned drawbacks, and in particular to provide catalysts for the selective hydrogenation of acetylenes and dienes in the gas phase, which give high activities and selectivities at low operating temperatures and make it possible to hydrogenate acetylene in $C_2$ streams without the use of moderators such as CO.

Accordingly, we have found a novel and improved supported palladium catalyst having a palladium content of from 0.001 to 2 wt %, in which palladium is present, substantially in the absence of promotor metal, in the form of a layer having a thickness of less than 5000 nm forming a shell around the support, wherein the palladium is applied in the form of a sol to a support by impregnation, or by spraying on to a heated support, and we have also found a method of using said catalysts for the hydrogenation of acetylenes and dienes.

The supported palladium catalysts of the invention have a content of palladium of from 0.001 to 2 wt %, preferably from 0.005 to 0.5 wt % and more preferably from 0.005 to 0.02 wt % and are substantially free from promotor metal, ie the catalysts contain from 0 to 1 wt %, preferably from 0 to 0.1 wt % and more preferably 0 wt % of promotor metal based on the amount of palladium, not including any foreign substances present in the palladium used. Furthermore, the layer thickness of the palladium in the supported palladium catalysts is less than 5000 nm, ie 10 to 4900 nm, preferably 50 to 4000 nm and more preferably 100 to 3500 nm, and said layer forms a shell around the support.

The supported palladium catalysts of the invention may be prepared as follows:

The preparation of the catalyst is carried out by spray-coating a hot support or impregnating a support with a preformed palladium sol.

The palladium sol can be prepared starting from palladium salts in which the palladium exists in oxidation stage 2 or 4. There may be used. eg, aqueous solutions of the chlorides, acetates, or nitrates of palladium, other palladium salts being possible; there is no restriction as to the anion. Suitable reducing agents that can be used are organic compounds such as ethanol, methanol, carboxylic acids and their alkali metal salts and also inorganic compounds such as $N_2H_4$ or $NaBH_4$. The particle size of the metal particles in the sol depends on the strength of the reducing agent used and on the metal salt used. Generally, stronger reducing agents are found to form smaller metal particles. The sols can be stabilized by the addition of organic polymers such as polyamines, poly(vinyl pyrrolidone) or polyacrylates. Alternatively, the preparation of the sol can be carried out by any other method described in the literature. Angew. Chemie, 103 (1991), pp 1344–1346 describes for example the preparation of stable metal sols by the reduction of metal salts with $(C_8H_{17})_4N^+[BEtH_3]$.

Suitable support materials are inorganic oxides such as $Al_2O_3$, $SiO_2$, $ZrO_2$, or $TiO_2$ and mixtures thereof. In particular, $Al_2O_3$ and $SiO_2$ have proven to be suitable.

Application of the sols to the support can be effected by various techniques to influence the distribution of the active component. In order to produce thin shells of active component across the entire cross-section of the extrudate the sol is sprayed on to an indirectly heated support. This is achieved by placing the supports in a rotatable disc pelletizer which is heated by a hot-air blower to temperatures between 80° and 200° C. While the disc is rotated the sol is spayed on to the supports via a dual-spray nozzle. Rotation of the disc ensures that there is thorough mixing of the support particles, eg. extrudates or chips. On contacting the hot support the liquid in the sol evaporates and the active component remains on the support. This method of application produces catalysts in which the active component is applied to the support in thin layers of less than 5 µm. The particle size of the noble metal agglomerate is generally of the same magnitude as in the sol. The catalyst is then dried at a temperature usually not exceeding 150° C.

Another technique for applying the active component consists in impregnating the supports with a sol according to its previously determined water uptake, which is substantially equivalent to its pore volume. After draining the support it is dried at a temperature usually not exceeding 150° C. Catalysts prepared in this manner surprisingly also contain the active component as a very thin layer. In this case, however, the active component is preferentially present in the macropores accessible from the outside, whilst in the technique involving spraying of the sol there is a substantially even distribution of the active component in the micropores and macropores. A substantial advantage of the impregnating and spraying techniques is that when the active component has been applied to the support via the sol, it already exists substantially in the reduced state. Thus there is no need to reduce the active component at high temperatures, which operation generally causes conglomeration of the active component by sintering and by this means reduces the catalytic surface area.

The catalysts of the invention have the advantage that they show higher selectivities and activities in the hydrogenation of acetylenes and dienes in the presence of large amounts of the corresponding mono-unsaturated compounds than do catalysts which have been prepared by impregnation of the support with a metal salt solution. Specifically, in $C_2$ hydrogenation they have the advantage of showing high selectivity without the introduction of CO, which often leads to complications in process engineering. A further advantage is that there is no need to add selectivity-improving but deactivating elements to act as promoters. A final advantage is that the catalysts prepared in accordance with the present invention and having $SiO_2$ or $Al_2O_3$ as support materials show equal activity and selectivity.

The selective hydrogenations of acetylenes and dienes are usually carried out in the gas phase at pressures of from 5 to 50 bar, preferably from 8 to 40 bar and more preferably from 10 to 30 bar, space velocities of from 1000 bis 5000 $m^3/m^3.h$, and temperatures ranging from 10° to 150° C., preferably 20° to 120° C. and more preferably 25° to 90° C. The number of reactors used depends on the concentration of the components to be hydrogenated present in the feed gas. In the case of acetylene and diene contents below 1% one adiabatic reactor suffices, the $H_2$:acetylene and/or diene ratio usually being approximately 1.1:1 to 2:1. This is by far the most usual case in the hydrogenation of acetylene. If the content of acetylenes and dienes is higher, the hydrogenation is carried out in two or more in-line reactors. In this case the hydrogen is usually fed in upstream of each reactor. The hydrogenation of a $C_3$ stream is mostly carried out in three in-line reactors, in the first of which a conversion of from 60 to 70% and in the second a conversion of from 30 to 40% is achieved. The third reactor is required for the residual conversion or serves as safety reactor. In the case of acetylene contents above 2% in a $C_2$ stream the hydrogenation is usually carried out in an isothermal reactor and one or two downstream adiabatic reactors.

Before the reactor is started it must usually be purged of oxygen by a stream of inert gas while it is slowly heated to 100° to 150° C. At this temperature the noble metal catalyst is usually reduced with $H_2$.

For carrying out performance tests, the catalysts may be used in non-pressurized laboratory equipment or in pilot equipment under elevated pressures of from 5 to 50 bar, preferably 10 to 30 bar. The inlet temperatures of the gas mixture formed in the hydrogenation zone are generally from 15° to 120° C., preferably from 25° to 90° C. The ratio by volume of hydrogen to the poly-unsaturated hydrocarbons is generally from 0.5:1 to 2.5:1, in $C_2$ hydrogenation preferably from 1.1:1 to 2:1 and more preferably from 1.2:1 to 1.8:1 and in the first stage of a $C_3$ hydrogenation from 0.6:1 to 0.9:1.

EXAMPLES

Example 1

Preparation of the catalyst

In order to prepare a stable Pd sol 2.165 g of $Pd(NO_3)_2$ and approximately 5 g of poly(vinyl pyrrolidone) were dissolved in 1000 mL of a 1:1 mixture of ethanol and water. The solution was stirred for 0.5 h at room temperature and then refluxed for 4 h. After cooling, there was obtained a palladium sol having a content of 1 g of Pd/L. 180 ml of this sol were diluted with 120 mL of distilled water to a volume of 300 mL. 300 g of an $Al_2O_3$ support having a total pore volume of 0.849 $cm^3/g$, a surface area (BET) of 357 $m^2/g$, and a water uptake of 1 mL/g were impregnated with the diluted sol over a period of 0.5 h and then dried, after draining, for 16 h at 120° C. After this drying period, the catalyst contained, as determined by analysis, 0.07 wt % of palladium based on the supported catalyst.

The resulting catalyst was tested for suitability in the selective hydrogenation of acetylene. To this end, a gas mixture of approximately 99% of ethylene and 1% of acetylene was passed through a fixed bed reactor over 29.1 g of the catalyst described above, at a temperature of 27° C. and under a pressure of 20 bar. The $H_2$:acetylene ratio was 1.12:1, the space velocity 3000 $h^{-1}$. Under these conditions there was achieved quantitative acetylene conversion at a selectivity toward acetylene of 66.0%.

Example 2

The catalyst of Example 1 also shows a very high selectivity toward ethylene when using a technique not carried out under pressure. To this end, there was passed a gas mixture of approximately 99% of ethylene and 1% acetylene through a fixed bed reactor over 14.0 g of the catalyst described above, at a temperature of 73° C. and under a pressure of 1 bar. The $H_2$:acetylene ratio was 1.11:1, the space velocity 3000 $h^{-1}$. Under these conditions there was achieved an acetylene conversion of 94.7% at a selectivity toward acetylene of 76.0%.

Example 3

Preparation of the Catalyst and the Selective Hydrogenation of Acetylene 1.603 g of a 11% strength $Pd(NO_3)_2$ solution were mixed with 1170 mL of bidistilled $H_2O$ and to the resulting solution there were added 5 g of poly(vinyl pyrrolidone). To this solution there were added 25 mL of a 0.8% strength hydrazine hydrate solution. It was stirred for 0.5 h at room temperature. The solution was then refluxed and stirred under reflux for 4 h. On cooling there was obtained a stable sol. 120 mL of this sol were diluted with bidistilled water to make 1 L. The diluted sol was sprayed on to 90 g of the $Al_2O_3$ support described in Example 1 in a heated disc pelletizer. The catalyst was dried for 16 h at 120° C. Analysis readings showed that this catalyst contained 0.009 wt % of Pd, based on the support.

The hydrogenation of acetylene was carried out as described in Example 2, the gas inlet temperature being, however, 87° C. and the $H_2$:$C_2H_2$ ratio being 1.82:1. There was achieved an acetylene conversion of 90.5% at a selectivity toward acetylene of 64.0%.

Example 4

Preparation of Catalyst and Selective $C_2$ Hydrogenation 1.365 g a 11% strength $Pd(NO_3)_2$ solution were mixed with 2.25 L of distilled $H_2O$ and to the solution there were added 1.5 g of poly(vinyl pyrrolidone). To this solution there were added 750 mL of ethanol and the solution was heated under reflux over a period of 4 h. On cooling, there was obtained a stable sol. 400 mL of this sol were diluted to a volume of 1 L. In a heated disc pelletizer, the diluted sol was sprayed on to 100 g of a $SiO_2$ support having a total pore area of 0.95 $cm^3/g$, a surface area (BET) of 136 $m^2/g$ and a water uptake of 1 mL/g. The catalyst was subsequently dried over a period of 16 h at 120° C.

The hydrogenation of acetylene was carried out as described in Example 2, the gas inlet temperature being, however, 82° C. and the $H_2$:$C_2H_2$ ratio 1.74:1. There was achieved an acetylene conversion of 85.1% at a selectivity toward acetylene of 66.8%.

At a gas inlet temperature of 92° C. and a $H_2$:$C_2H_2$ ratio of 1.72:1, an acetylene conversion of 98.2% at a selectivity toward acetylene of 46.4% was achieved.

Example 5

114 mL of a $7.4 \times 10^{-3}$M $PdCl_2$ solution were mixed with 1304 mL of bidistilled $H_2O$. To this solution there were added 5 g of poly(vinyl pyrrolidone) and 180 mL of a 0.034M sodium citrate solution. The reaction solution was heated under reflux for 4 h. On cooling, there was obtained a stable sol. In a heated disc pelletizer, 1110 mL of this sol were sprayed on to 92.5 g of the $SiO_2$ support described in Example 3. The catalyst was then dried for 16 h at 120° C. The palladium content of this catalyst was shown by analysis to be 0.06 wt % of Pd.

The hydrogenation of acetylene was carried out as described in Example 2, the gas inlet temperature being however 87° C. and the $H_2$:$C_2H_2$ ratio 1.76:1. There was achieved an acetylene conversion of 90.5% at a selectivity toward acetylene of 54.3%.

Example 6

To 0.909 g of a 11 wt % strength $Pd(NO_3)_2$ solution there were added 760 mL of bidistilled $H_2O$ and 0.5 g of poly (vinyl amine). To this solution there were added 240 mL of a 0.034M sodium formate solution. The reaction solution was heated under reflux over a period of 4 h. On cooling, there was obtained a stable sol. 200 mL of this sol were diluted to a volume of 1 L. In a heated disc pelletizer, the diluted sol was sprayed on to 113 g of the $Al_2O_3$ support described in Example 1. The catalyst was subsequently dried for 16 h at 120° C.

The hydrogenation of acetylene was carried out as described in Example 2, the gas inlet temperature being however 97° C. and the $H_2$:$C_2H_2$ ratio 1.78:1. There was achieved an acetylene conversion of 92.1% at a selectivity toward acetylene of 49.2%.

Example 7

To 27.27 g of a 11 wt % strength solution of $Pd(NO_3)_2$ there were added 495 mL of bidistilled $H_2O$ and 5 g of poly(vinyl pyrrolidone). To this solution there were added 495 mL of ethanol and the mixture was stirred under reflux over a period of 4 h. On cooling, there was obtained a stable sol. 30 mL of this sol were diluted with distilled $H_2O$ to a volume of 300 mL. 100 of the $SiO_2$ support described in Example 3 were impregnated over a period of 0.5 h with the diluted sol and then dried, following draining, over a period of 16 h at 120° C. The palladium content of the catalyst was shown by analysis to be 0.035 wt % of Pd, based on the support.

The hydrogenation of acetylene was carried out as described in Example 1, the gas inlet temperature being however 63° C. and the $H_2$:$C_2H_2$ ratio 1.76:1. There was achieved an acetylene conversion of 82.0% at a selectivity toward acetylene of 52.7%.

Example 8

For the preparation of a stable Pd sol there were dissolved 0.373 g of Pd acetate and approximately 5 g of poly(vinyl pyrrolidone) in 1170 mL of water. To this solution there were added dropwise 25 mL of a 0.8% hydrazine hydrate solution with vigorous stirring. The reaction solution was subsequently refluxed over a period of 2 h. On cooling, there was obtained a stable palladium sol having a content of 0.15 g of Pd per liter. In a heated disc pelletizer, 400 mL of this sol were sprayed on to 100 g of a $SiO_2$ support having a total pore area of 0.95 $cm^3/g$, a surface area (BET) of 136 $m^2/g$, and a water uptake of 1 mL/g. The catalyst was then dried for 16 h at 120° C.

Example 9

$C_3$ Hydrogenation in the Gas Phase

The catalyst prepared in the previous example was used in a test for the gas phase hydrogenation of methyl acetylene and propadiene in a $C_3$ stream coming from a steam cracker. The process conditions simulated the conditions of a first stage of the usually three-stage methyl acetylene/propadiene hydrogenation in a $C_3$ stream. In an adiabatic tubular reactor (diameter 20 mm) there were placed 70 mL of the catalyst of Example 8. After purging with nitrogen and treatment with hydrogen at 120° C., 650 L/h of a gas mixture having the following composition: 5.2% of propane, 1.7% of propadiene, and 2.4% of methyl acetylene in propylene, and 21 L/h of hydrogen were passed over the catalyst at an inlet temperature of 60° C. and a pressure of 10 bar. The effluent consisted of 6.4% of propane, 0.42% of propadiene, 0.31% of methyl acetylene in propylene. This indicates a selectivity toward propylene of 79% at a conversion of 70%.

We claim:

1. A supported palladium catalyst having a palladium content of from 0.001 to 2 wt % in which palladium has been applied from a sol to a porous inorganic oxide support, substantially free of any promoter metal, to provide a layer having a thickness of less than 5000 nm forming a shell around said porous support.

2. A supported palladium catalyst as claimed in claim 1, wherein the palladium is applied by impregnating the support with a preformed aqueous sol of said palladium and subsequently drying at a temperature not to exceed about 150° C.

3. A supported palladium catalyst as defined in claim 1, wherein the support used is $Al_2O_3$, $SiO_2$, $ZrO_2$, $TiO_2$, or a mixture thereof.

4. A supported palladium catalyst as defined in claim 1, wherein the support used is $Al_2O_3$, $SiO_2$, or a mixture thereof.

5. A supported palladium catalyst as claimed in claim 1, wherein the layer thickness of the applied palladium is less than 5,000 nm.

6. A supported palladium catalyst as claimed in claim 1, wherein the palladium is applied by spray-coating said support which has been preheated to a temperature of between 80° and 200° C. with a preformed aqueous palladium sol such that the water evaporates on contact with the hot support.

7. A process as claimed in claim 6, wherein said palladium as the active component is applied to the support in thin layers of less than 5 µm, the palladium particles having a particle size of the about same magnitude as in the sol.

8. A process as claimed in claim 1, wherein the applied layer of the palladium has a thickness of from 50 to 4000 nm.

9. A process as claimed in claim 1, wherein the applied layer of the palladium has a thickness of from 100 to 3500 nm.

10. A process as claimed in claim 2, wherein said porous oxide support has both macropores and micropores and said impregnation followed by drying preferentially coats the macropores accessible from the outside with the active palladium catalyst.

11. A process as claimed in claim 10, wherein said porous oxide support has both macropores and micropores and said spray-coating produces a substantially even coating of both the macroporous and microporous surfaces with the active palladium catalyst.

* * * * *